United States Patent [19]
Jameson et al.

[11] Patent Number: 5,962,634
[45] Date of Patent: Oct. 5, 1999

[54] IGE ANTAGONISTS

[75] Inventors: Bradford A. Jameson, Philadelphia, Pa.; Brian J. Sutton, Kennington, United Kingdom; James M. McDonnell, Philadelphia, Pa.; Hannah J. Gould, London, United Kingdom; Robert Korngold, Cherry Hill, N.J.; Andrew J. Beavil, Gravesend, United Kingdom

[73] Assignees: Thomas Jefferson University, Philadelphia, Pa.; King's College, London, United Kingdom

[21] Appl. No.: 08/765,536

[22] PCT Filed: Jun. 30, 1995

[86] PCT No.: PCT/US95/08401

§ 371 Date: Apr. 30, 1997

§ 102(e) Date: Apr. 30, 1997

[87] PCT Pub. No.: WO96/01643

PCT Pub. Date: Jan. 25, 1996

Related U.S. Application Data

[63] Continuation-in-part of application No. 08/271,943, Jul. 8, 1994, abandoned.

[51] Int. Cl.$^6$ .................................................... C07K 7/00
[52] U.S. Cl. .................... 530/324; 530/325; 530/326; 530/327; 530/328; 530/329; 530/330; 514/12; 514/13; 514/14; 514/15; 514/16; 514/17; 514/18; 514/885
[58] Field of Search .................... 530/324–330; 514/12–18, 885

[56] References Cited

U.S. PATENT DOCUMENTS 5,292,867  3/1994  Chang .................................. 530/387.3

FOREIGN PATENT DOCUMENTS 0488979   6/1992   European Pat. Off. .
9106570   5/1991   WIPO .

OTHER PUBLICATIONS

HCAPLUS DN 118:192247, Ball et al., *Int. S. Pept. Protein Res.*, 40(5), 370–9, 1992.

Claman et al., "Immunoglobulin Dysregulation in Murine Graft–vs–Host Disease: A Hyper–IgE Syndrome", *Clin. Imm. Immunopath.*, 1990, 56, 46–53.

Korngold et al., "Variable Capacity of L3T4$^{30}$ T Cells to Cause Lethal Graft–Versus–Host Disease Across Minor Histocompatibility Barriers in Mice", *J. Exp. Med.*, 1987, 165, 1552–1564.

Merrifield, "Solid Phase Peptide Synthesis. I. The Synthesis of a Tetrapeptide", *J. Am. Chem. Soc.*, 1963, 15, 2149–2154.

Beavil et al., "Structural Basis of the IgE–Fc∈RI Interaction", *Biochem. Soc. Trans.*, 1993, 21, 968–972.

Murphy et al., "Role of Mast Cells in Early Epithelial Target Cell Injury in Experimental Acute Graft–Versus–Host Disease", *J. Invest. Derma.*, 1994, 102, 451–461.

Nissim et al., "Fine Specificity of the IgE Interaction with the Low and High Affinity Fc Receptor", *J. Immunol.*, 1993, 150, 1365–1374.

Wang et al., "Epidermal Langherhans Cells from Normal Human Skin Bind Monomeric IgE via Fc∈RI", *J. Exp. Med.*, 1992, 175, 1353–1365.

HCAPLUS DN: 118:122551, McDunnell et al., *J. of Immunol.*, 149(5), 1626–30, 1992.

HCAPLUS DN 116:35978, Miller et al., *Arch. Biochem. Biophys.*, 291(1). 69–75, 1991.

HCAPLUS DN 115:156552, Childerstone et al., *J. Immunol.*, 146(5), 1463–9, 1991.

HCAPLUS DN 111:149428. Thompson et al., *J. Biol. Chem.*, 264(19), 11511–20, 1989.

*Primary Examiner*—Cecilia J. Tsang
*Assistant Examiner*—C. Delacroix-Muirheid
*Attorney, Agent, or Firm*—Woodcock Washburn Kurtz Mackiewicz & Norris LLP

[57] ABSTRACT

The present invention relates to methods for modulating interaction between IgE and Fc∈R1. The present invention also relates to compounds that modulate IgE binding to Fc∈R1.

29 Claims, 6 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 193 amino acids
      (B) TYPE: amino acid
      (D) TOPOLOGY: linear (ii) MOLECULE TYPE: protein (xi) SEQUENCE DESCRIPTION: SEQ ID NO:1:

```
Glu Ser Pro Thr Leu Leu Cys Val Ala Leu Leu Phe Phe Ala Pro Asp
1               5                   10                  15

Gly Val Leu Ala Val Pro Gln Lys Pro Lys Val Ser Leu Asn Pro Pro
                20                  25                  30

Trp Asn Arg Ile Phe Lys Gly Glu Asn Val Thr Leu Thr Cys Asn Gly
            35                  40                  45

Asn Asn Phe Phe Glu Val Ser Ser Thr Lys Trp Phe His Asn Gly Ser
        50                  55                  60

Leu Ser Glu Glu Thr Asn Ser Ser Leu Asn Ile Val Met Ala Lys Phe
65                  70                  75                  80

Glu Asp Ser Gly Glu Tyr Lys Cys Gln His Gln Gln Val Asn Glu Ser
                85                  90                  95

Glu Pro Val Tyr Leu Glu Val Phe Ser Asp Trp Leu Leu Leu Gln Ala
                100                 105                 110

Ser Ala Glu Val Val Met Glu Gly Gln Pro Leu Phe Leu Arg Cys His
            115                 120                 125

Gly Trp Arg Met Trp Asp Val Tyr Lys Val Ile Tyr Tyr Lys Asp Gly
        130                 135                 140
```

```
        Glu Ala Leu Lys Tyr Trp Tyr Glu Asn His Asn Ile Ser Ile Thr Asn
        145                 150                 155                 160

Ala Thr Val Glu Asp Ser Gly Thr Tyr Tyr Cys Thr Gly Lys Val Trp
                        165                 170                 175

Gln Leu Asp Tyr Glu Ser Glu Pro Leu Asn Ile Thr Val Ile Lys Ala
                    180                 185                 190

Pro (2) INFORMATION FOR SEQ ID NO:2:

(i) SEQUENCE CHARACTERISTICS:
        (A) LENGTH: 174 amino acids
        (B) TYPE: amino acid
        (D) TOPOLOGY: linear (ii) MOLECULE TYPE: protein (xi) SEQUENCE DESCRIPTION: SEQ ID NO:2:

Asp Ser Gly Thr Val Trp Gly Ala Leu Gly His Gly Ile Asn Leu Asn
        1               5                   10                  15

Ile Pro Asn Gly Gln Met Thr Asp Ile Asp Glu Val Arg Trp Glu
                        20                  25                  30

Arg Gly Ser Thr Leu Val Ala Glu Glu Lys Arg Lys Met Lys Pro Phe
                    35                  40                  45

Leu Lys Ser Gly Ala Phe Glu Ile Leu Ala Asn Gly Asp Leu Lys Ile
        50                  55                  60

Lys Asn Leu Thr Arg Asp Asp Ser Gly Thr Tyr Asn Val Thr Val Tyr
        65                  70                  75                  80

Ser Thr Asn Gly Thr Arg Ile Leu Asn Lys Ala Leu Asp Leu Arg Ile
                        85                  90                  95

Leu Glu Met Val Ser Lys Pro Met Ile Tyr Trp Glu Cys Ser Asn Ala
                        100                 105                 110

Thr Leu Thr Cys Glu Val Leu Glu Gly Thr Asp Val Glu Leu Lys Leu
                    115                 120                 125

Tyr Gln Gly Lys Glu His Leu Arg Ser Leu Arg Gln Lys Thr Met Ser
                    130                 135                 140

Tyr Gln Trp Thr Asn Leu Arg Ala Pro Phe Lys Cys Lys Ala Val Asn
        145                 150                 155                 160

Arg Val Ser Gln Glu Ser Glu Met Glu Val Val Asn Cys Pro
                        165                 170

(2) INFORMATION FOR SEQ ID NO:3:

(i) SEQUENCE CHARACTERISTICS:
        (A) LENGTH: 11 amino acids
        (B) TYPE: amino acid
        (D) TOPOLOGY: both (ii) MOLECULE TYPE: peptide (xi) SEQUENCE DESCRIPTION: SEQ ID NO:3:

Ile Tyr Tyr Lys Asp Gly Glu Ala Leu Lys Tyr
        1               5                   10

(2) INFORMATION FOR SEQ ID NO:4:

(i) SEQUENCE CHARACTERISTICS:
        (A) LENGTH: 19 amino acids
        (B) TYPE: amino acid
        (D) TOPOLOGY: both
```

```
      (ii) MOLECULE TYPE: peptide (xi) SEQUENCE DESCRIPTION: SEQ ID NO:4:

Thr Tyr Tyr Cys Thr Gly Lys Val Trp Gln Leu Asp Tyr Glu Ser Glu
      1               5                  10                  15

Pro Leu Asn (2) INFORMATION FOR SEQ ID NO:5:

(i) SEQUENCE CHARACTERISTICS:
        (A) LENGTH: 6 amino acids
        (B) TYPE: amino acid
        (D) TOPOLOGY: both (ii) MOLECULE TYPE: peptide (xi) SEQUENCE DESCRIPTION: SEQ ID NO:5:

Lys Val Trp Gln Leu Asp
      1               5

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: both (ii) MOLECULE TYPE: peptide (xi) SEQUENCE DESCRIPTION: SEQ ID NO:6:

Cys Ile Tyr Tyr Lys Asp Gly Glu Ala Leu Lys Tyr Cys
      1               5                  10
```

IGE ANTAGONISTS

CROSS-REFERENCE TO RELATED APPLICATIONS

This application is the U.S. National Phase of PCT/US95/08401, filed Jun. 30, 1995, and a Continuation In Part of U.S. Ser. No. 08/271,943, filed Jul. 8, 1994, abandoned.

FIELD OF THE INVENTION

The present invention relates to biologically active compounds which are similar to regions of the high affinity Fc receptor for immunoglobulin E.

BACKGROUND OF THE INVENTION

Clinical bone marrow transplantation is an important therapeutic treatment for several diseases including high risk leukemia, aplastic anemia, and severe combined immunodeficiency. In addition, there is a wide range of metabolic and genetic disorders that can potentially be corrected by this approach. However, the usefulness of marrow transplantation is currently limited by several important risk factors, the principal one being graft-versus-host disease (GVHD), an often times lethal complication which occurs in a high proportion of transplants.

The risk of GVHD can be reduced by HLA matching of the marrow donor and recipient, with a matched sibling being the primary choice. Yet, less than 30% of the patients in North America have an HLA-matched sibling, and therefore must seek suitable unrelated HLA-matched donors from the National Marrow Donor Program. The probability of finding an unrelated HLA-matched donor is currently on the order of 30–40% and depend on the total number of donors registered. In both related and unrelated HLA-matched transplant situations, the risk of GVHD is still quite high due to disparity of non-HLA multiple minor histocompatibility (H) antigens. GVHD is somewhat higher in unrelated cases, as this increases the probability of differences at these loci.

Mature donor T cells contaminating the marrow inoculum are responsible for GVHD. Several studies have shown that depletion of these T cells significantly diminishes the incidence of disease. However, the elimination of donor T cells has also resulted in a greater incidence of leukemic relapse. It seems important to provide at least some level of T cell immunocompetency in these completely immunocompromised patients to not only combat residual leukemia cells but also to counter opportunistic infections. In this respect, the same GVHD-reactive donor T cells may be important for targeting leukemia cells expressing the same host allogeneic histocompatibility antigens. Therapeutic approaches that could ameliorate the pathogenic tissue destruction accompanying GVHD, particularly in the gut and skin, but that would allow for continued anti-leukemia activity would greatly benefit marrow transplant patients.

Immediate allergic responses, also referred to as type 1 hypersensitivity reactions, are mediated through the interaction of immunoglobulin E (IgE) with the α-chain of its high affinity Fc receptor, FcεR1. The binding of a multivalent allergen to an IgE-FcεR1complex initiates a cross-linking of the receptor and consequent cellular activation. These high affinity receptors are found primarily on mast cells and basophils. When activated by an allergen, these cells respond by releasing histamine, eicosanoids and cytokines.

In addition to its high affinity Fc receptor, IgE binds to a low affinity receptor, the FcεR2, which is found on B cells, T cells, macrophages, NK cells, eosinophils, platelets, follicular dendritic cells as well as several other cell types. Activation of the FcεR2 has been implicated in IgE-dependent cell cytotoxicity (ADCC) as well as in allergic inflammation.

Many different fine mapping studies have been conducted on the binding of the IgE to its Fc receptors. The consensus mapping data is confirmed by a recent study by Nissim et al. (1993) *J. Immunol.* 150: 1365–1374, which is incorporated herein by reference, showing that the binding activity for both the high and low affinity receptors resides within the Cε3 (the third constant domain) of the IgE. Data show that the species specific binding of IgE to the FcεR1 is contained within the first 16 amino acids of the CE3, whereas no species specific binding is observed in the same region with respect to binding the FcεR2.

There is a need for compounds and methods which can inhibit IgE-FcεR1 interaction. IgE-FcεR1 interaction is associated with immediate allergic reactions. There is a need for compounds and methods which can inhibit mast cell and basophil activity that results from IgE-FcεR1 interaction. Mast cell and basophil activity linked to IgE-FcεR1 interaction is associated, for example with reactions to allergens and GVHD. Identification of compounds that inhibit the IgE-FcεR1 interaction can be used in methods of treating allergies and GVHD.

SUMMARY OF THE INVENTION

The present invention relates to peptides that modulate IgE binding to FcεR1 and that consist of 4–50 amino acids and comprise at least a fragment of SEQ ID NO:3 of at least 4 amino acids.

The present invention relates to pharmaceutical compositions comprising a peptide that modulate IgE binding to FcεR1and that consist of 4–50 amino acids and comprises at least a fragment of SEQ ID NO:3 of at least 4 amino acids and a pharmaceutically acceptable carrier or diluent.

The present invention relates to peptides that modulate IgE binding to FcεR1 and that consist of 6–50 amino acids and comprise SEQ ID NO:5.

The present invention relates to pharmaceutical compositions comprising a peptide that modulate IgE binding to FcεR1and that consist of 6–50 amino acids and comprise SEQ ID NO:5 and a pharmaceutically acceptable carrier or diluent.

The present invention relates to a method of inhibiting IgE binding to FcεR1on cells comprising the steps of contacting cells that contain the FcεR1 with a peptide that inhibits IgE binding to FcεR1 and that consists of 4–50 amino acids and comprises at least a fragment of SEQ ID NO:3 of at least 4 amino acids in an amount sufficient to inhibit IgE binding to FcεR1.

The present invention relates to a method of inhibiting IgE binding to FcεR1 on cells comprising the steps of contacting cells that contain the FcεR1 with a peptide that inhibits IgE binding to FcεR1 and that consists of 6–50 amino acids and comprises SEQ ID NO:5 in an amount sufficient to inhibit IgE binding to FcεR1.

The present invention relates to a method of therapeutically or prophylactically treating an individual suffering from or susceptible to an immediate allergic response comprising administering to such an individual an effective amount of a peptide that inhibits IgE binding to FcεR1 and that consists of 4–50 amino acids and comprises at least a fragment of SEQ ID NO:3 of at least 4 amino acids in an amount sufficient to inhibit IgE binding to FcεR1.

The present invention relates to a method of therapeutically or prophylactically treating an individual suffering from or susceptible to an immediate allergic response comprising administering to such an individual an effective amount of a peptide that inhibits IgE binding to FcεR1 and that consists of 6–50 amino acids and comprises SEQ ID NO:5 in an amount sufficient to inhibit IgE binding to FcεR1.

The present invention relates to a peptide dimer that modulate IgE binding to FcεR1 comprising a first monomer which consists of between 4 and 50 amino acids and comprises at least a fragment of SEQ ID NO:3 of at least 4 amino acids, and a second monomer which consists of between 6 and 50 amino acids and comprises SEQ ID NO:5.

DESCRIPTION OF PREFERRED EMBODIMENTS

Figure 1:
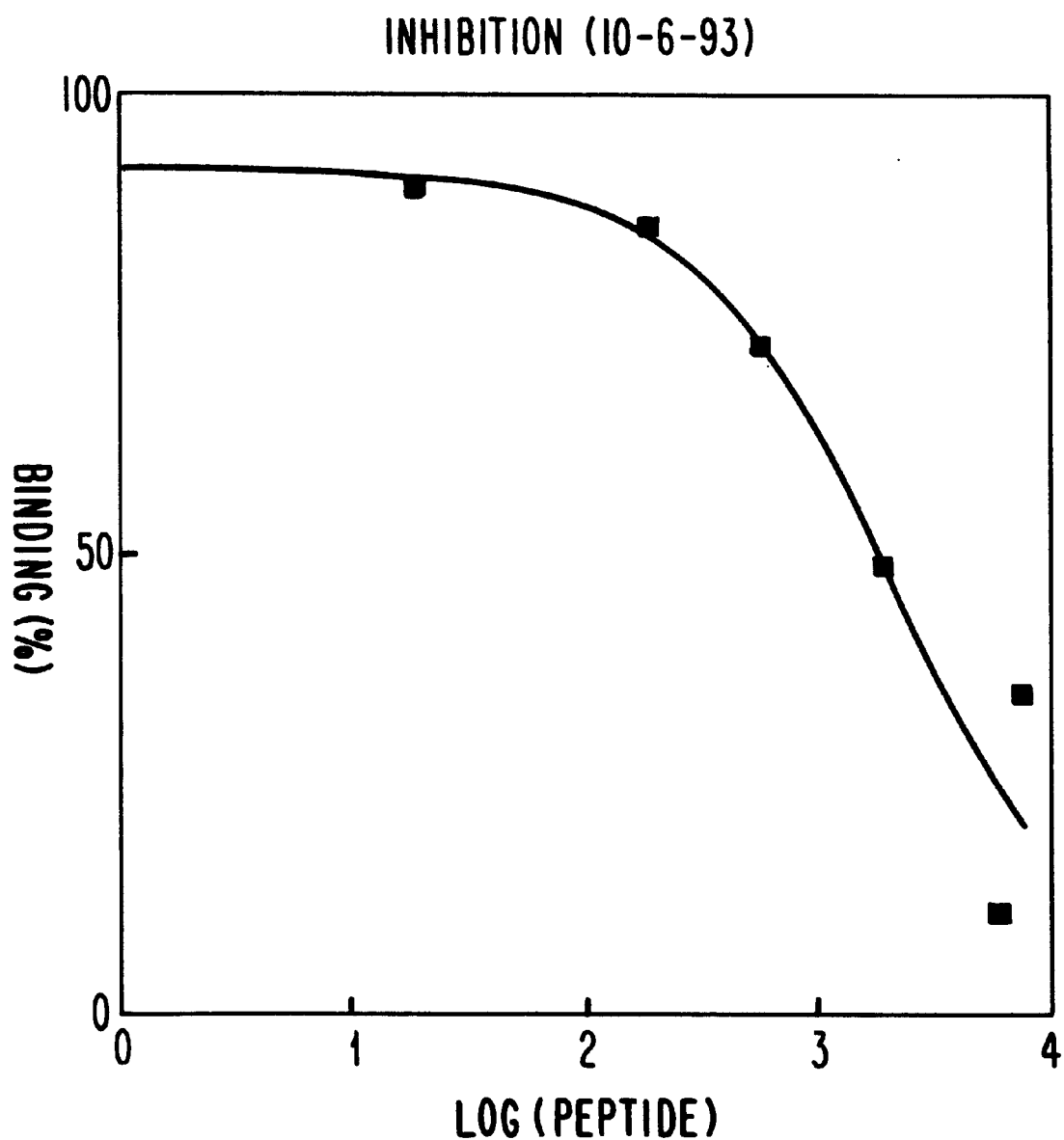
FIG. 1 shows data from in vitro experiments testing the effect of various concentrations of D amino acid peptide #1, which is described in Example 3, on the level of inhibition of IgE-IgE receptor.

The present invention provides conformationally restrained analogs which are modelled from the FcεR1 α-chain surface. This application is related to U.S. patent application Ser. No. 08/271,943 which is incorporated in its entirety herein by reference. Using commercially available molecular modeling software, a structural model of the α-chain of the IgE high affinity receptor was created using the known three-dimensional coordinates of related proteins (See Beavil, A. J. et al. 1993 *Biochem. Soc. Trans.* 21: 968–972, which is incorporated herein by reference). CD2 was chosen as the principal template because its three dimensional structure was known and it shares significant sequence homology with the IgE- receptor protein.

The compounds of the invention are capable of inhibiting IgE-IgE receptor binding linked to immediate allergic responses. The compounds of the invention intervene in the IgE-IgE receptor signal pathway and, thereby, creating therapeutic reagents for the treatment of IgE-dependent disease states including allergic rhinitis, food allergies, atropic dermatitis and allergic asthma.

The amino acid sequence of FcεR1 is shown in SEQ ID NO:1. The amino acid sequence of CD2 is shown in SEQ ID NO:2. The known three dimensional structure of CD2 was used as a template. The FcεR1 amino acid sequence shown in SEQ ID NO:1 was aligned to the three dimensional CD2 template. Alignment of the sequences allowed for a prediction of the three dimensional structure of FcεR1. The FcεR1 IgE-binding region in the α-chain sequence was identified using the predicted three dimensional structure. The modeled structure of the α-chain of the high affinity IgE receptor, in turn, was used as a template in selecting and designing peptides, particularly conformationally restrained analogs of the receptor surface.

The location of a principal IgE-binding region in the α-chain of FcεR1 occurs between amino acids 140 and 160 (134–154 of SEQ ID NO:1), more particularly between amino acids 144–154 (139–149 of SEQ ID NO:1) of the FcεR1 protein sequence. The amino acid sequence 144–154 (139–149 of SEQ ID NO:1) is shown as SEQ ID NO:3.

According to some embodiments, the peptides of the invention that inhibit IgE from binding to FcεR1 consist of 4–50 amino acids and comprise at least a fragment of SEQ ID NO:3 of at least 4 amino acids.

In some preferred embodiments, the peptides of the invention consist of 4–25 amino acids including at least a fragment of SEQ ID NO:3 of at least 4 amino acids. In some embodiments, the peptide of the invention consist of 6–20 amino acids including at least a fragment of SEQ ID NO:3 of at least 4 amino acids. In some embodiments, the peptide of the invention consist of 8–15 amino acids including at least a fragment of SEQ ID NO:3 of at least 4 amino acids. In some embodiments, the peptides of the invention consist of 10–12 amino acid residues including at least a fragment of SEQ ID NO:3 of at least 4 amino acids.

As used herein, the term "fragment of SEQ ID NO:3" is meant to refer to peptides which comprise an amino acid sequence identical to a portion of SEQ ID NO:3 having at least 4. In some embodiments, peptides that comprise a fragment of SEQ ID NO:3 include fragments of SEQ ID NO:3 having 4, 5, 6, 7, 8, 9 or 10. Accordingly, a fragment of SEQ ID NO:3 of at least 4 amino acids may be have amino acids 1–4, 2–5, 3–6, 4–7, 5–8, 6–9, 7–10, 8–11, 1–5, 2–6, 3–7, 4–8, 5–9, 6–10, 7–11, 1–6, 2–7, 3–8, 4–9, 5–10, 6–11, 1–7, 2–8, 3–9, 4–10, 5–11, 1–8, 2–9, 3–10, 4–11, 1–9, 2–10, 3–11, 1–10 or 2–11 of SEQ ID NO:3. Peptides may comprise SEQ ID NO:3. Thus, a peptide of the invention that comprises at least a fragment of SEQ ID NO:3 of at least 4 amino acids may comprise SEQ ID NO:3 or a fragment thereof such as one that has amino acids 1–4, 2–5, 3–6, 4–7, 5–8, 6–9, 7–10, 8–11, 1–5, 2–6, 3–7, 4–8, 5–9, 6–10, 7–11, 1–6, 2–7, 3–8, 4–9, 5–10, 6–11, 1–7, 2–8, 3–9, 4–10, 5–11, 1–8, 2–9, 3–10, 4–11, 1–9, 2–10, 3–11, 1–10 and 2–11 of SEQ ID NO:3. In some preferred embodiments, the peptides of the invention comprise SEQ ID NO:3. In some preferred embodiments, the peptides comprise a fragment of SEQ ID NO:3 that consists of 4–10 amino acids. In some embodiments, the peptides comprise a fragment of SEQ ID NO:3 that consists of 6–10 amino acids. In some embodiments, the peptides comprise a fragment of SEQ ID NO:3 that consists of 8–10 amino acids.

In addition to SEQ ID NO:3 or fragments thereof, peptides of the invention may comprise at least a fragment of SEQ ID NO:3 of at least 4 amino acids and further comprise additional amino acids. The additional amino acids may be FcεR1 amino acids, non-FcεR1 amino acids or both. FcεR1 amino acids include amino acids 140–143 (amino acids 134–137 of SEQ ID NO:1) or fragments thereof, amino acids 155–160 (amino acids 149–154 of SEQ ID NO:1) or fragments thereof. Additional FcεR1 amino acids include adjacent amino acid sequences. Moreover, peptides may comprise other FcεR1 amino acid sequences such as those which define other IgE-FcεR1 binding regions. Non-FcεR1 amino acids include amino acids used to conformationally restrict the peptide.

In some preferred embodiments, peptides are conformationally constrained and consist of amino and carboxy terminal cysteines flanking SEQ ID NO:3 or a fragment thereof selected from the group consisting of amino acids 1–4, 2–5, 3–6, 4–7, 5–8, 6–9, 7–10, 8–11, 1–5, 2–6, 3–7, 4–8, 5–9, 6–10, 7–11, 1–6, 2–7, 3–8, 4–9, 5–10, 6–11, 1–7, 2–8, 3–9, 4–10, 5–11, 1–8, 2–9, 3–10, 4–11, 1–9, 2–10, 3–11, 1–10 or 2–11 of SEQ ID NO:3. One or more residues of such peptides may be a D amino acid. Peptides may be biotinylated. The amino acid sequences described herein may be constructed to proceed in sequence from the amino terminus to carboxy terminus or from the carboxy terminus to the amino terminus. When the sequence proceeds from the amino terminus to carboxy terminus, it is usually constructed of L amino acids. In some embodiments, it is constructed of all L amino acids except either an N terminal cysteine or a C terminal cysteine which is a D amino acid. When D amino acids are used to construct the compound, the sequence is usually reversed from the order it occurs as an L amino acid peptide. It therefore proceeds from the carboxy terminus to the amino terminus. In some embodiments, it is constructed of all D amino acids except either an N terminal cysteine or a C terminal cysteine which is an L amino acid.

The location of another IgE-binding region of FCεR1 occurs between amino acids 168–186 of SEQ ID NO:1, more particularly between amino acids 174–179 of SEQ ID NO:1. The amino acid sequence 168–186 of SEQ ID NO:1 is shown as SEQ ID NO:4. The amino acid sequence 174–179 of SEQ ID NO:1 is shown as SEQ ID NO:5.

In some embodiments, the peptides of the invention that inhibit IgE from binding to FcεR1 consist of 6–50 amino acids and comprises SEQ ID NO:5.

In some preferred embodiments, the peptides of the invention consist of 6–25 amino acids including SEQ ID NO:5. In some embodiments, the peptides consist of 6–20 amino acids including SEQ ID NO:5. In some embodiments, the peptides consist of 8–15 amino acids including SEQ ID NO:5. In some embodiments, the peptides consist of 10–12 amino acids including SEQ ID NO:5.

In some embodiments, peptides of the invention which comprise SEQ ID NO:5 may comprise SEQ ID NO:4 or a fragment of SEQ ID NO:4 of at least 6 amino acids including SEQ ID NO:5. As used herein, the term "fragment of SEQ ID NO:4 of at least 6 amino acids including SEQ ID NO:5" is meant to refer to peptides which comprise an amino acid sequence identical to a portion of SEQ ID NO:4 having at least 6 including amino acids 7–12 of SEQ ID NO:4. Amino acids 7–12 of SEQ ID NO:4 are SEQ ID NO:5. In some embodiments, peptides that comprise a fragment of SEQ ID NO:4 having at least 6 amino acids including SEQ ID NO:5 include fragments of SEQ ID NO:4 having 6, 7, 8, 9, 10, 11, 12, 13, 14, 15, 16, 17, 18 or 19 amino acids. Accordingly, a fragment of SEQ ID NO:4 of at least 6 amino acids including SEQ ID NO:5 may be have amino acids 7–12, 7–13, 7–14, 7–15, 7–16, 7–17, 7–18, 7–19, 6–12, 6–13, 6–14, 6–15, 6–16, 6–17, 6–18, 6–19, 5–12, 5–13, 5–14, 5–15, 5–16, 5–17, 5–18, 5–19, 4–12, 4–13, 4–14, 4–15, 4–16, 4–17, 4–18, 4–19, 3–12, 3–13, 3–14, 3–15, 3–16, 3–17, 3–18, 3–19, 2–12, 2–13, 2–14, 2–15, 2–16, 2–17, 2–18, 2–19, 1–12, 1–13, 1–14, 1–15, 1–16, 1–17, 1–18 or 1–19 of SEQ ID NO:4. Peptides may comprise SEQ ID NO:4. Thus, a peptide of the invention that comprises at least a fragment of SEQ ID NO:4 of at least 6 amino acids including SEQ ID NO:5 may comprise SEQ ID NO:4 or a fragment thereof such as one that has amino acids 7–12, 7–13, 7–14, 7–15, 7–16, 7–17, 7–18, 7–19, 6–12, 6–13, 6–14, 6–15, 6–16, 6–17, 6–18, 6–19, 5–12, 5–13, 5–14, 5–15, 5–16, 5–17, 5–18, 5–19, 4–12, 4–13, 4–14, 4–15, 4–16, 4–17, 4–18, 4–19, 3–12, 3–13, 3–14, 3–15, 3–16, 3–17, 3–18, 3–19, 2–12, 2–13, 2–14, 2–15, 2–16, 2–17, 2–18, 2–19, 1–12, 1–13, 1–14, 1–15, 1–16, 1–17, 1–18 and 1–19 of SEQ ID NO:4. In some preferred embodiments, the peptides comprise a fragment of SEQ ID NO:4 that consists of 6–10 amino acids including SEQ ID NO:5. In some embodiments, the peptides comprise a fragment of SEQ ID NO:4 that consists of 6–10 amino acids including SEQ ID NO:5. In some embodiments, the peptides comprise a fragment of SEQ ID NO:4 that consists of 8–10 amino acids including SEQ ID NO:5.

In addition to SEQ ID NO:5 or fragments of SEQ ID NO:4 that comprise SEQ ID NO:5, according to some embodiments, peptides of the invention may comprise additional amino acids. The additional amino acids may be FcεR1 amino acids, non-FcεR1 amino acids or both. Additional FcεR1 amino acids include adjacent amino acid sequences such as amino acids 150–167 and 187–200 of SEQ ID NO:1 or fragments thereof. Moreover, peptides may comprise other FcεR1 amino acid sequences such as those which define other IgE-FcεR1 binding regions. Non-FcεR1amino acids include amino acids used to conformationally restrict the peptide.

In some preferred embodiments, peptides are conformationally constrained and consist of amino and carboxy terminal cysteines flanking SEQ ID NO:4 or a fragment thereof selected from the group consisting of amino acids 7–12, 7–13, 7–14, 7–15, 7–16, 7–17, 7–18, 7–19, 6–12, 6–13, 6–14, 6–15, 6–16, 6–17, 6–18, 6–19, 5–12, 5–13, 5–14, 5–15, 5–16, 5–17, 5–18, 5–19, 4–12, 4–13, 4–14, 4–15, 4–16, 4–17, 4–18, 4–19, 3–12, 3–13, 3–14, 3–15, 3–16, 3–17, 3–18, 3–19, 2–12, 2–13, 2–14, 2–15, 2–16, 2–17, 2–18, 2–19, 1–12, 1–13, 1–14, 1–15, 1–16, 1–17, 1–18 or 1–19 of SEQ ID NO:4. One or more residues of such peptides may be a D amino acid. Peptides may be biotinylated. The amino acid sequences described herein may be constructed to proceed in sequence from the amino terminus to carboxy terminus or from the carboxy terminus to the amino terminus. When the sequence proceeds from the amino terminus to carboxy terminus, it is usually constructed of L amino acids. In some embodiments, it is constructed of all L amino acids except either an N terminal cysteine or a C terminal cysteine which is a D amino acid. When D amino acids are used to construct the compound, the sequence is usually reversed from the order it occurs as an L amino acid peptide. It therefore proceeds from the carboxy terminus to the amino terminus. In some embodiments, it is constructed of all D amino acids except either an N terminal cysteine or a C terminal cysteine which is an L amino acid.

According to some embodiments of the invention, peptide dimers are provided which comprise two different monomeric subunits, one of which is a peptide of the invention that comprises at least a fragment of SEQ ID NO:3 of at least 4 amino acids and the other of which is a peptide of the invention which comprises SEQ ID NO:5. Dimeric peptides of the invention inhibit IgE from binding to FcεR1 and comprise one monomer that consists of 4–50 amino acids including at least a fragment of SEQ ID NO:3 of at least 4 amino acids, and one monomer that consists of 6–50 amino acids including SEQ ID NO:5.

Dimers according to the invention comprise two monomeric subunits linked to each other by non-peptide bonds. In some preferred dimers, each of the monomeric subunits has a cysteine residue at at least one terminus and the dimer is formed by disulfide bonds which form between a terminal cysteines of each monomer. In some preferred dimers, the monomeric subunits are linked by other covalent bonds between terminal residues. Methods of linking monomers to form dimers are well known to those having ordinary skill in the art.

In some embodiments, the amino terminal of the monomer that comprises at least a fragment of SEQ ID NO:3 is linked to the amino terminal of the monomer that comprises SEQ ID NO:5. In some embodiments, the amino terminal of the monomer that comprises at least a fragment of SEQ ID NO:3 is linked to the carboxy terminal of the monomer that comprises SEQ ID NO:5. In some embodiments, the carboxy terminal of the monomer that comprises at least a fragment of SEQ ID NO:3 is linked to the amino terminal of the monomer that comprises SEQ ID NO:5. In some embodiments, the carboxy terminal of the monomer that comprises at least a fragment of SEQ ID NO:3 is linked to the carboxy terminal of the monomer that comprises SEQ ID NO:5.

In preferred embodiments of the invention which relate to dimers, the monomer that comprises at least a fragment of SEQ ID NO:3 of at least 4 amino acids consists of 4–25 amino acids. In some embodiments, the monomer that comprises at least a fragment of SEQ ID NO:3 consists of 6–20 amino acids. In some embodiments, the monomer that comprises at least a fragment of SEQ ID NO:3 consists of 8–15 amino acids. In some embodiments, the monomer that comprises at least a fragment of SEQ ID NO:3 consists of 10–12 amino acid residues.

In preferred embodiments of the invention which relate to dimers, the monomer that comprises at least a fragment of SEQ ID NO:3 of at least 4 amino acids comprises SEQ ID NO:3 or a fragment thereof such as one that has amino acids 1–4, 2–5, 3–6, 4–7, 5–8, 6–9, 7–10, 8–11, 1–5, 2–6, 3–7, 4–8, 5–9, 6–10, 7–11, 1–6, 2–7, 3–8, 4–9, 5–10, 6–11, 1–7, 2–8, 3–9, 4–10, 5–11, 1–8, 2–9, 3–10, 4–11, 1–9, 2–10, 3–11, 1–10 and 2–11 of SEQ ID NO:3.

In preferred embodiments of the invention which relate to dimers, the monomer that comprises SEQ ID NO:5 consists of 6–25 amino acids. In some embodiments, the monomer which comprises SEQ ID NO:5 consists of 6–20 amino acids. In some embodiments, the monomer that comprises SEQ ID NO:5 consists of 8–15 amino acids. In some embodiments, the monomer which comprises SEQ ID NO:5 consists of 10–12 amino acid residues.

In preferred embodiments of the invention which relate to dimers, the monomer that comprises SEQ ID NO:5 comprises SEQ ID NO:4 or a fragment thereof such as one that has amino acids 7–12, 7–13, 7–14, 7–15, 7–16, 7–17, 7–18, 7–19, 6–12, 6–13, 6–14, 6–15, 6–16, 6–17, 6–18, 6–19, 5–12, 5–13, 5–14, 5–15, 5–16, 5–17, 5–18, 5–19, 4–12, 4–13, 4–14, 4–15, 4–16, 4–17, 4–18, 4–19, 3–12, 3–13, 3–14, 3–15, 3–16, 3–17, 3–18, 3–19, 2–12, 2–13, 2–14, 2–15, 2–16, 2–17, 2–18, 2–19, 1–12, 1–13, 1–14, 1–15, 1–16, 1–17, 1–18 and 1–19 of SEQ ID NO:4.

In preferred embodiments of the invention which relate to dimers, the monomer that comprises at least a fragment of SEQ ID NO:3 consists of 4–25 amino acids and the monomer that comprises SEQ ID NO:5 consists of 6–25 amino acids. In some embodiments, the monomer that comprises at least a fragment of SEQ ID NO:3 of at least 4 amino acids consists of 6–20 amino acids and the monomer which comprises SEQ ID NO:5 consists of 6–20 amino acids. In some embodiments, the monomer that comprises at least a fragment of SEQ ID NO:3 of at least 4 amino acids consists of 8–15 amino acids and the monomer that comprises SEQ ID NO:5 consists of 8–15 amino acids. In some embodiments, the monomer that comprises at least a fragment of SEQ ID NO:3 of at least 4 amino acids consists of 10–12 amino acid residues and the monomer which comprises SEQ ID NO:5 consists of 10–12 amino acid residues.

In some preferred embodiments of the invention which relate to dimers, the monomer that comprises at least a fragment of SEQ ID NO:3 of at least 4 amino acids comprises SEQ ID NO:3 or a fragment thereof such as one that has amino acids 1–4, 2–5, 3–6, 4–7, 5–8, 6–9, 7–10, 8–11, 1–5, 2–6, 3–7, 4–8, 5–9, 6–10, 7–11, 1–6, 2–7, 3–8, 4–9, 5–10, 6–11, 1–7, 2–8, 3–9, 4–10, 5–11, 1–8, 2–9, 3–10, 4–11, 1–9, 2–10, 3–11, 1–10 and 2–11 of SEQ ID NO:3 and the monomer that comprises SEQ ID NO:5 comprises SEQ ID NO:4 or a fragment thereof such as one that has amino acids 7–12, 7–13, 7–14, 7–15, 7–16, 7–17, 7–18, 7–19, 6–12, 6–13, 6–14, 6–15, 6–16, 6–17, 6–18, 6–19, 5–12, 5–13, 5–14, 5–15, 5–16, 5–17, 5–18, 5–19, 4–12, 4–13, 4–14, 4–15, 4–16, 4–17, 4–18, 4–19, 3–12, 3–13, 3–14, 3–15, 3–16, 3–17, 3–18, 3–19, 2–12, 2–13, 2–14, 2–15, 2–16, 2–17, 2–18, 2–19, 1–12, 1–13, 1–14, 1–15, 1–16, 1–17, 1–18 and 1–19 of SEQ ID NO:4.

According to some embodiments of the invention, peptides that inhibit IgE from binding to FcεR1 are provided which comprise at least a fragment of SEQ ID NO:3 of at least 4 amino acids and which further comprises SEQ ID NO:5. More particularly, in some embodiments of the invention, peptides comprise 10–100 amino acids including at least a fragment of SEQ ID NO:3 of at least 4 amino acids and SEQ ID NO:5.

In some preferred embodiments of the invention, the peptides, which include at least a fragment of SEQ ID NO:3 of at least 4 amino acids and SEQ ID NO:5, comprise 10–50 amino acids including at least a fragment of SEQ ID NO:3 having 4–11 amino acids and at least a fragment of SEQ ID NO:4 having 6–19 amino acids including SEQ ID NO:5. In some embodiments, the peptides, which include at least a fragment of SEQ ID NO:3 of at least 4 amino acids and SEQ ID NO:5, comprise 12–40 amino acids including at least a fragment of SEQ ID NO:1 of 6–20 amino acids including 6–11 amino acids from SEQ ID NO:3. In some embodiments, the peptide, which include at least a fragment of SEQ ID NO:3 of at least 4 amino acids and SEQ ID NO:5, comprise 14–30 amino acids including at least a fragment of SEQ ID NO:1 of 8–15 amino acids including 8–11 amino acids from SEQ ID NO:3. In some embodiments, the peptide, which include at least a fragment of SEQ ID NO:3 of at least 4 amino acids and SEQ ID NO:5, comprises 16–25 amino acids including at least a fragment of SEQ ID NO:1 of 11–12 amino acids including SEQ ID NO:3. In some embodiments, the peptide, which include at least a fragment of SEQ ID NO:3 of at least 4 amino acids and SEQ ID NO:5, comprises 12–40 amino acids including SEQ ID NO:5. In some embodiments, the peptide, which include at least a fragment of SEQ ID NO:3 of at least 4 amino acids and SEQ ID NO:5, comprises 14–30 amino acids including SEQ ID NO:5. In some embodiments, the peptide, which include at least a fragment of SEQ ID NO:3 of at least 4 amino acids and SEQ ID NO:5, comprises 16–25 amino acids including SEQ ID NO:5. In some embodiments, the peptide, which include at least a fragment of SEQ ID NO:3 of at least 4 amino acids and SEQ ID NO:5, comprises SEQ ID NO:3 or a fragment thereof such as one that has amino acids 1–4, 2–5, 3–6, 4–7, 5–8, 6–9, 7–10, 8–11, 1–5, 2–6, 3–7, 4–8, 5–9, 6–10, 7–11, 1–6, 2–7, 3–8, 4–9, 5–10, 6–11, 1–7, 2–8, 3–9, 4–10, 5–11, 1–8, 2–9, 3–10, 4–11, 1–9, 2–10, 3–11, 1–10 and 2–11 of SEQ ID NO:3 linked to SEQ ID NO:5 comprises SEQ ID NO:4 or a fragment thereof such as one that has amino acids 7–12, 7–13, 7–14, 7–15, 7–16, 7–17, 7–18, 7–19, 6–12, 6–13, 6–14, 6–15, 6–16, 6–17, 6–18, 6–19, 5–12, 5–13, 5–14, 5–15, 5–16, 5–17, 5–18, 5–19, 4–12, 4–13, 4–14, 4–15, 4–16, 4–17, 4–18, 4–19, 3–12, 3–13, 3–14, 3–15, 3–16, 3–17, 3–18, 3–19, 2–12, 2–13, 2–14, 2–15, 2–16, 2–17, 2–18, 2–19, 1–12, 1–13, 1–14, 1–15, 1–16, 1–17, 1–18 and 1–19 of SEQ ID NO:4.

In some embodiments, the peptide which includes the sequence which is defined as at least a fragment of SEQ ID NO:3 of at least 4 amino acids at the amino terminal portion of the sequence relative to the position of the portion of the sequence that comprises SEQ ID NO:5.

In some embodiments, the peptide which includes the sequence SEQ ID NO:5 at the amino terminal portion of the sequence relative to the position of the portion of the sequence that which is defined as the sequence that comprises at least a fragment of SEQ ID NO:3 of at least 4 amino acids.

Peptides of the invention inhibit IgE from binding to FcεR1. The ability of a peptide to inhibit IgE from binding to FcεR1 may be determined by one having ordinary skill in the art by performing binding assays which are in vitro and/or in vivo assays using readily available starting materials. For example, assays to determine whether a peptide has biological activity are described in Examples 1 and 2. Briefly, an in vitro assay is described which allows one to determine whether or not IgE is inhibited from binding to FcεR1. An in vivo assay is described which allows one to determine whether or not GVHD occurs in a bone marrow transplant model. GVHD is linked to IgE dysregulation and to mast cell activity (Claman and Spiegelberg 1990 *Clin. Imm. Immunopath.* 56: 46–53; and Murphy et al. 1994 *J. Invest. Derma.* 102: 451–461). Accordingly, inhibition of IgE-FcεR1 binding in vivo will prevent the lethal effects of GVHD in the in vivo assay. The ability of a compound of the invention to inhibit IgE from binding to FcεR1 IgE refers its possession of IgE-FcεR1binding inhibition activity in an IgE-FcεR1 binding assay.

In some embodiments, peptides of the present invention comprise D amino acids. As used herein, the term "D amino acid peptides" is meant to refer to peptides according to the present invention which comprise at least one and in some embodiments a plurality of D amino acids. D amino acid peptides inhibit IgE from binding to FcεR1, thus retaining the biological activity of peptides having L amino acid sequences. The use of D amino acid peptides is desirable as they are less vulnerable to degradation and therefore have a longer half life. D amino acid peptides comprising mostly all or consisting of D amino acids may comprise amino acid sequences in the reverse order of SEQ ID NO:3 or fragments or derivatives thereof or SEQ ID NO:4 or fragments thereof.

In some embodiments, peptides of the present invention are conformationally restricted to present and maintain the proper structural conformation for biological activity. The compositions may comprise additional amino acid residues required to achieve proper three dimensional conformation including residues which facilitate circularization or desired folding. Accordingly, in preferred embodiments, cysteine residues are added to the terminal residues of peptides comprising SEQ ID NO:3 or fragments thereof or SEQ ID NO:4 of fragments thereof including SEQ ID NO:5. Formation of disulfide bonds between the terminal cysteines results in a circularized, i.e. cyclic peptides.

D amino acid residues may be provided to facilitate conformational restriction. For example, in order to facilitate disulfide bond formation and stability, a D amino acid cysteine may be provided at one or both termini.

Peptides which fall within the structural definition provided herein may be produced by those having ordinary skill in the art using routine techniques and readily available starting materials without undue experimentation. One having ordinary skill in the art can then test the peptides to determine whether or not they inhibit IgE binding to FcεR1 and are thus peptides of the invention.

It is also contemplated that some embodiments of the invention include the peptides that comprise at least a fragment of a derivative of SEQ ID NO: 3 of at least 4 amino acids rather than a fragment of SEQ ID NO:3 and/or a derivative of SEQ ID NO:5 rather than SEQ ID NO:5. As used herein, the term "derivative of SEQ ID NO:3" is meant to refer to a peptide which comprises an amino acid sequence substantially identical to SEQ ID NO:3. As used herein, the term "derivative of SEQ ID NO:5" is meant to refer to a peptide which comprises an amino acid sequence substantially identical to SEQ ID NO:5. As used herein, the term "substantially identical to SEQ ID NO:3 or a fragment thereof" refers to an amino acid sequence that is the same as the amino acid sequence of SEQ ID NO:3 or a fragment thereof except some of the residues are deleted, substituted with conservative amino acids or additional amino acids are inserted. As used herein, the term "substantially identical to SEQ ID NO:5" refers to an amino acid sequence that is the same as the amino acid sequence of SEQ ID NO:5 except some of the residues are deleted, substituted with conservative amino acids or additional amino acids are inserted. Those having ordinary skill in the art can readily design and produce derivatives having substantially identical amino acid sequences of SEQ ID NO:3 or a fragment thereof or SEQ ID NO:5 with deletions and/or insertions and/or conservative substitutions of amino acids. For example, following what are referred to as Dayhof's rules for amino acid substitution (Dayhof, M. D. (1978) *Nat. Biomed. Res. Found.*, Washington, D.C. Vol. 5, supp. 3), amino acid residues in a peptide sequence may be substituted with comparable amino acid residues. Such substitutions are well known and are based the upon charge and structural characteristics of each amino acid. Derivatives include fragments of SEQ ID NO:3 or SEQ ID NO:5 with deletions and/or insertions and/or conservative substitutions.

Peptides may be synthesized by well known techniques such as the solid-phase synthetic technique initially described by Merrifield, in *J. Am. Chem. Soc.,* 15: 2149–2154 (1963). Other peptide synthesis techniques may be found, for example, in M. Bodanszky et al., (1976) *Peptide Synthesis*, John Wiley & Sons, 2d Ed.; Kent and Clark-Lewis in *Synthetic Peptides in Biology and Medicine*, p. 295–358, eds. Alitalo, K., et al. Science Publishers, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984), which is incorporated herein by reference. The synthesis of peptides by solution methods may also be used, as described in *The Proteins*, Vol. II, 3d Ed., p. 105–237, Neurath, H. et al., Eds., Academic Press, New York, N. Y. (1976). Appropriate protective groups for use in such syntheses will be found in the above texts, as well as in J. F. W. McOmie, *Protective Groups in Organic Chemistry*, Plenum Press, New York, N.Y. (1973), which is incorporated herein by reference.

In general, these synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention is preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Peptides may also be prepared by recombinant DNA techniques. Provision of a suitable DNA sequence encoding the desired peptide permits the production of the peptide using recombinant techniques now known in the art. The coding sequence can be obtained from natural sources or synthesized or otherwise constructed using widely available starting materials by routine methods. When the coding DNA is prepared synthetically, advantage can be taken of known codon preferences of the intended host where the DNA is to be expressed.

To produce peptides of the invention, one having ordinary skill in the art can, using well known techniques, synthesize or obtain a DNA molecule encoding SEQ ID NO:1 or portions thereof which include SEQ ID NO:3 or a fragment thereof or SEQ ID NO:5 from readily available human DNA and insert that DNA molecule into a commercially available expression vector for use in well known expression systems. Including in these systems are those in which the peptide of interest is produced as a fusion protein.

For example, the commercially available plasmid pSE420 (Invitrogen, San Diego, Calif.) may be used for recombinant production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in mammalian cells such as Chinese Hamster Ovary cells.

One having ordinary skill in the art may use these or other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign bacteria. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionein promoter can be induced by the addition of heavy metal ions.

In some embodiments, a DNA molecule that includes a nucleotide sequence which encodes the peptide of the invention is synthesized using the amino acid sequence information herein and the genetic code. Those having ordinary skill in the art can readily synthesize DNA molecules that include nucleotide sequences which encode the peptides of the invention using codons preferred by a desired host cell. The DNA molecule that is generated may be inserted in an expression vector which allows for very high levels of expression, sometimes referred to as overexpression, in a desired host.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate the protein that is produced.

In addition to peptides, the present invention contemplates compounds which display substantially the same surface as the peptides of the invention. Such compounds, referred to as mimetics, are not peptides but comprise a similar surface as the peptides and can thus interact with other molecules in a similar fashion as the peptides of the invention. By providing a similar surface involved in intermolecular interactions, mimetics perform essentially the same function by essentially the same means to achieve essentially the same result as the peptides of the invention.

The present invention relates to a method of therapeutically or prophylactically treating an individual suffering from or susceptible to an immediate allergic response. Those having ordinary skill in the art can readily identify individuals suspected of suffering from or being susceptible to an immediate allergic response conditions such as response is selected from the group consisting of: graft versus host disease, allergic rhinitis, food allergies, atropic dermatitis and allergic asthma. In the case of GVHD, treatment may be provided prophylactically in conjunction with transplantation procedure or in response to symptoms associated with GVHD. Those with ordinary skill in the art could readily identify individuals for whom administration of the peptides of the invention would be beneficial to alleviate or prevent immediate allergy response conditions.

The method of therapeutically or prophylactically treating an individual suffering from or susceptible to an immediate allergic response comprises administering to said individual an effective amount of a peptide according to the invention. A prophylactically effective amount is an amount which is effective to prevent or decrease the immediate allergic response in an individual susceptible to such a reaction without causing lethal side effects on the individual. A prophylactically effective amount is an amount which is effective to decrease or eliminate the immediate allergic response in an individual suffering from such a reaction without causing lethal side effects on the individual. Those having ordinary skill in the art can readily and routinely determine the ranges of both prophylactically and therapeutically effective amounts of the peptides of the invention without undue experimentation.

It is contemplated that the present invention is useful to therapeutically or prophylactically treat individuals suspected of suffering from or being susceptible to reactions are mediated through the interaction of immunoglobulin E (IgE) with the α-chain of its high affinity Fc receptor, FcεR1.

The present invention provides pharmaceutical compositions that comprise the peptides of the invention and pharmaceutically acceptable carriers or diluents. The pharmaceutical composition of the present invention may be formulated by one having ordinary skill in the art. Suitable pharmaceutical carriers are described in Remington's Pharmaceutical Sciences, A. Osol, a standard reference text in this field, which is incorporated herein by reference. In carrying out methods of the present invention, conjugated compounds of the present invention can be used alone or in combination with other diagnostic, therapeutic or additional agents. Such additional agents include excipients such as coloring, stabilizing agents, osmotic agents and antibacterial agents.

For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the active agent to reach the targeted cells. These methods include, but are not limited to, oral, topical, intradermal, subcutaneous, intravenous, intramuscular and intraparenteral modes of administration. The compounds may be administered singly or in combination with other compounds. The compounds of the invention are preferably administered with a pharmaceutically acceptable carrier selected on the basis of the selected route of administration and standard pharmaceutical practice.

The dosage administered varies depending upon factors such as: pharmacodynamic characteristics; its mode and route of administration; age, health, and weight of the recipient; nature and extent of symptoms; kind of concurrent treatment; and frequency of treatment. Usually, the dosage of peptide can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily 8 to 800 milligrams are administered to an individual per day in divided doses 1 to 6 times a day or in sustained release form is effective to obtain desired results.

EXAMPLES

Example 1

In vitro Inhibition of Binding of IgE Fc to Fcε by Biosensor Assay

Figure 4:
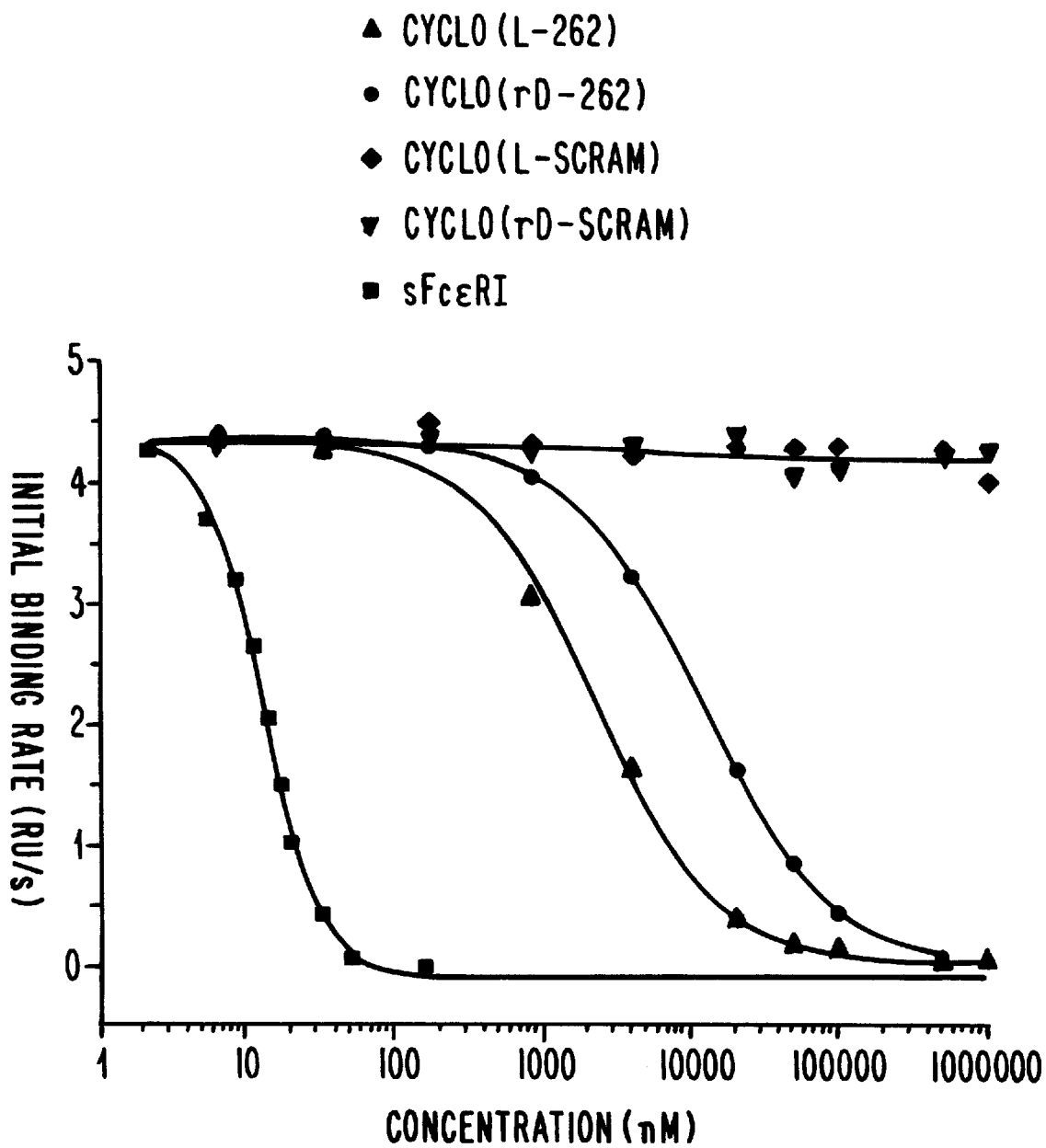
FIG. 4 shows the in vitro inhibition of binding of IgE Fc to Fcε by biosensor assay.

The kinetics of IgE Fc binding to soluble Fcε were determined using a BIAcore biosensor (Pharmacia Biosensor AB, Uppsala, Sweden). The FcεRIα was immobilized via primary amine groups to a carboxymethylated dextran-coated CM5 sensor chip, at a concentration of 80 $\mu$g/ml in 10 mM sodium acetate buffer pH 4.5, using N-hydroxysuccinimide and N-ethyl-N'-(3-diethyl-aminopropyl)-carbodiimide (Pharmacia Amine Coupling Kit). Free sites were blocked with 1M ethanolamine-HCl pH 8.5. Binding of peptides to IgE was measured by the ability of peptides to prevent binding of IgE to the immobilized FcεRIα. Various concentrations of peptide were incubated with a fixed concentration of IgE (10 nM) and allowed to equilibrate for 24 h. The peptide-IgE mixtures were injected over the sensor surface, in 10 mM HEPES buffered saline (HBS) with 150 mM NaCl, 3.4 mM EDTA and 0.005% surfactant P20 (Pharmacia), at 25° C., using conditions under which binding is limited by mass transport rather than by kinetic parameters. This allowed measurement of the concentration of free IgE, and thus the solution association constant ($K_a$) for the receptor-ligand interaction. The initial rate of IgE binding to the immobilized receptor is presented as a function of peptide concentration in FIG. 4.

Example 2

In vivo Test to Identify IgE-IgE Receptor Binding Inhibitors

The transplantation of B10.D2 CD4+ T-cells along with T-cell-depleted bone marrow has been shown previously to induce a lethal GVHD response in irradiated (850 cGy) DBA/2 mice (Korngold and Sprent (1987) *J. Exp. Med.* 165:1552–1564, which is incorporated herein by reference). In addition, in this strain combination dermal mast cells are believed to be involved in the early stages of cutaneous GVHD development. The transplantation of $7 \times 10^6$ B10.D2 CD4+ T-cells resulted in a 100% incidence of lethal GVHD in DBA/2 recipients with a median survival time of 9 days. Transplantation of donor T-cell-depleted bone marrow alone resulted in complete survival out to termination of the experiment at 70 days. To determine the ability of an L form and a reverse D form of a test compound of the invention to inhibit IgE-IgE receptor binding and thereby inhibit GVHD, DBA/2 recipients of B10.D2 CD4+ T-cells are treated on days 0 and 3 with 0.5 mg of either test compound i.v. Incidence of survival and median survival time are compared to an untreated group and a group treated with a scrambled reverse D form of the test compound. These data indicate that the ability of a reverse D test compound to effect the development of GVHD and alloreactivity of transplanted donor T-cells.

Example 3

In one embodiment of the invention, a peptide that includes SEQ ID NO:3 and that is restrained by cysteines at each end is synthesized. The peptide and has the following sequence:

C-I-Y-Y-K-D-G-E-A-L-K-Y-$C^D$, where the carboxy terminal cysteine is a "D" amino acid. This D amino acid peptide is referred to herein as D amino acid peptide #1. D amino acid peptide #1 consists of a total of 13 amino acids and comprises all of SEQ ID NO:3. D amino acid peptide #1 is conformationally restricted using two terminal cysteines to form a disulfide bond which cyclicizes the peptide. The D amino acid cysteine is included to facilitate the formation and stability of the disulfide bond.

Approximately $0.5 \times 10^6$ transfected CHO cells were incubated with a mixture of 5 nM labelled myeloma IgE and D amino acid peptide #1 was titrated at various concentrations for 1 h at room temperature. Non-specific bindings were determined by pre-incubating the cells with a 100-fold excess of rat IgE. After incubation, the cells were separated from the unbound iodinated IgE by 2 min. centrifugation through mixed oils. The cell pellets were then counted in a 5500 Beckman gamma counter.

Concentration of the D amino acid peptide #1 used ranged form $9.324 \times 10^{-8}$M to $3.73 \times 10^{-5}$M. The $IC_{50} = 5.14 \times 10^{-6}$M. The results are shown on FIG. 1.

Figure 2:
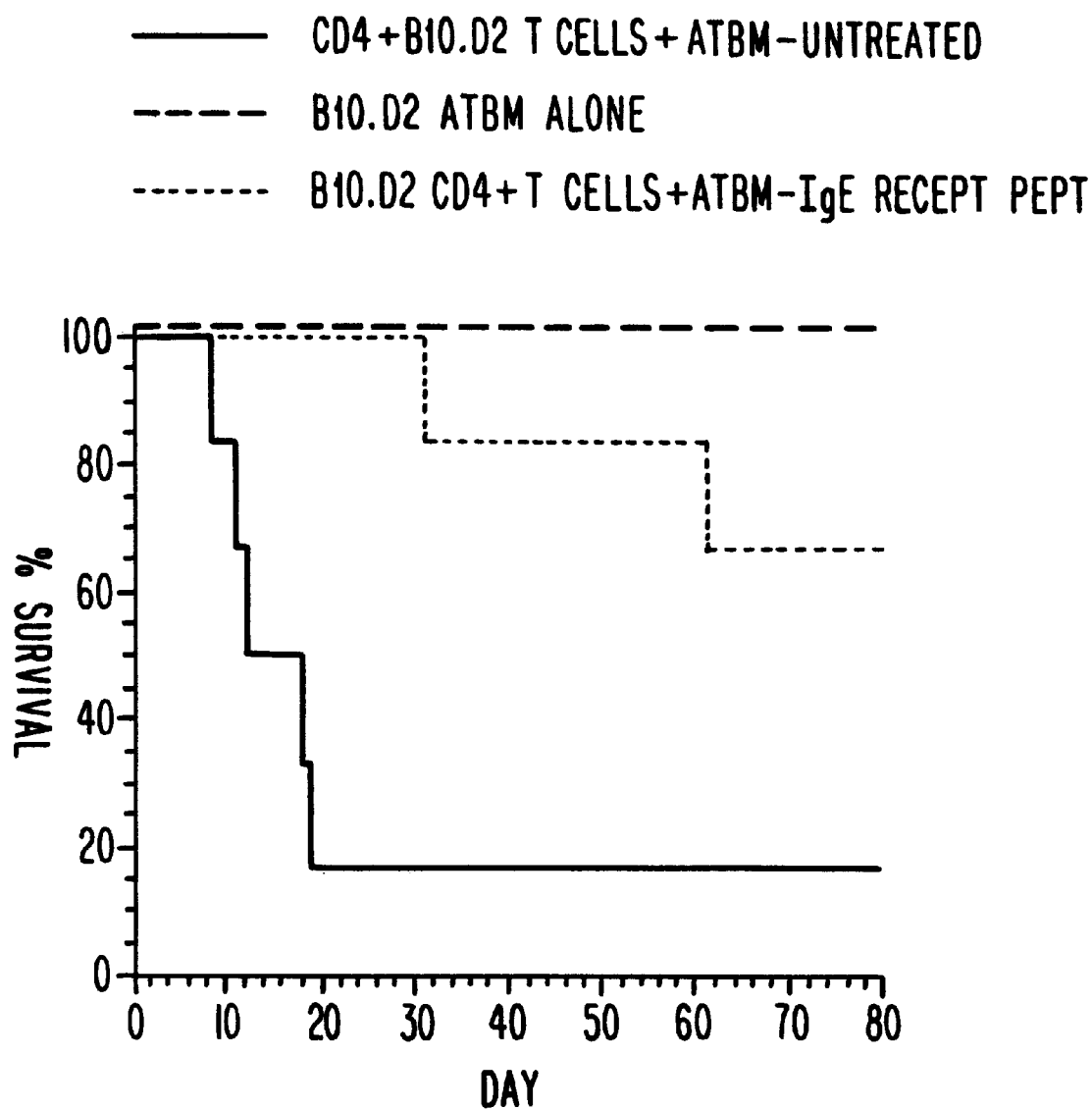
FIG. 2 shows data from in vivo experiments testing the effect of D amino acid peptide #1, which is described in Example 3, on survival of mice in a GVHD model.

As shown in FIG. 2, the transplantation of $2 \times 10^6$ B10.D2 CD4+ T cells resulted in an 83% incidence of lethal GVHD in DBA/2 recipients with a median survival time of 15 days. Transplantation of donor T-cell-depleted bone marrow alone resulted in complete survival out to termination of the experiment at 80 days. DBA/2 recipients of B10.D2 CD4+ T cells and treated on days 0 and 3 with 0.5 mg D amino acid peptide #1 i.v. exhibited a significantly higher incidence of survival (67%) and a significantly prolonged median survival time of greater than 80 days (p=0/04), compared to the untreated group. This data indicates that the IgE receptor analogs of the invention can diminish the development of GVHD and alloreactivity of transplanted donor T cells.

Example 4

Surface Plasmon Resonance Experiment

The kinetics of binding of IgE Fc to soluble FcεR1α were determined using a BIAcore biosensor (Pharmacia Biosensor AB, Uppsala, Sweden). The FcεR1α was immobilized via primary amine groups to a carboxymethylated dextran-coated CM5 sensor chip, at a concentration of 85 µg/ml in 10mM sodium acetate buffer pH 4.5, using N-hydroxy-succinimide and N-ethyl-N'-(3-diethyl-aminopropyl)-carbodiimide. Free sites were blocked with 1M ethanolamine-hydrochloride pH 8.5.

Figure 3:
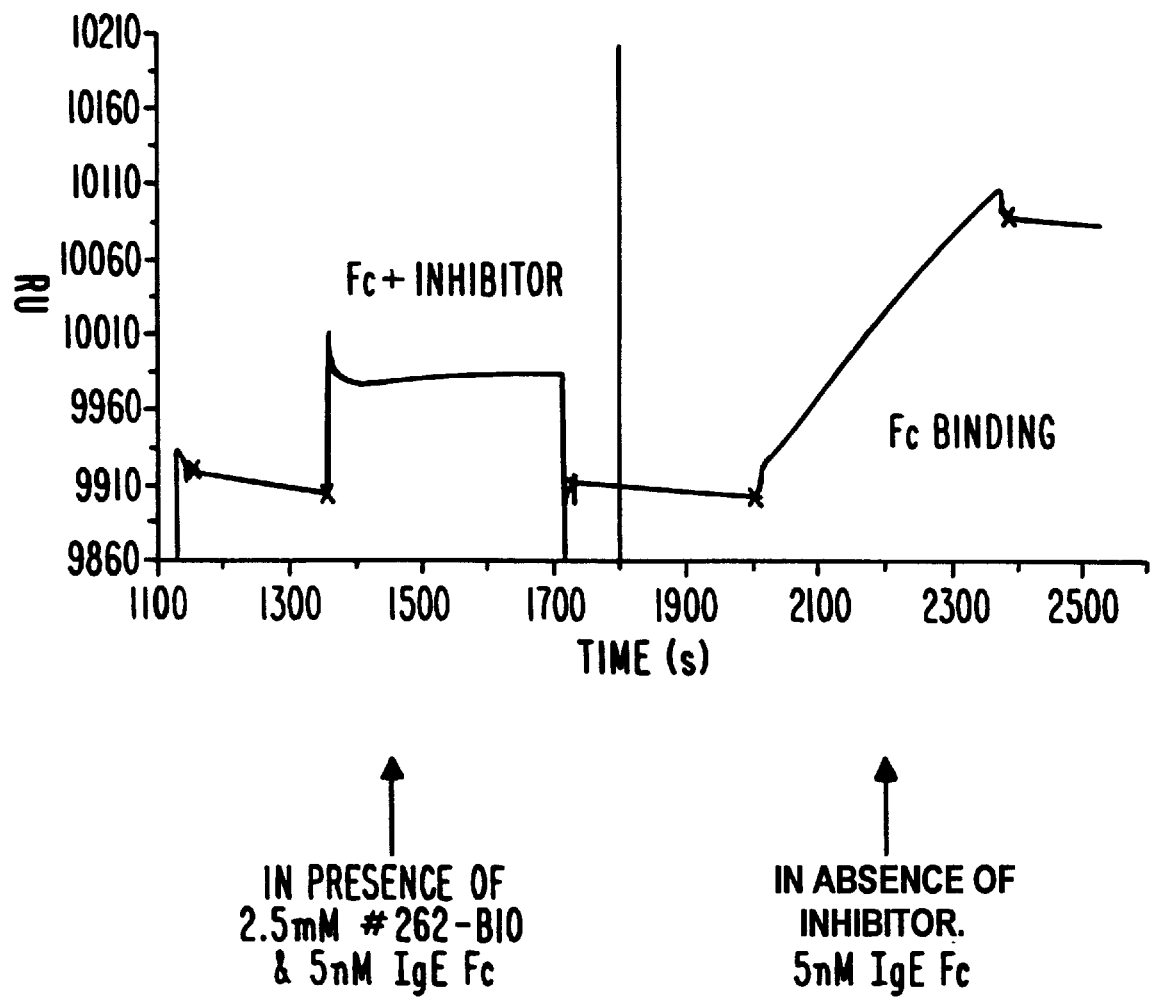
FIG. 3 shows data from inhibition assays using a biosensor in which the association of IgE-Fc at a concentration of 5nM was monitored for 6 minutes in the presence at various concentrations and absence of a biotinylated derivative of the D amino acid peptide #1, which is described in Example 3.

The association of IgE-Fc at a concentration of 5nM was monitored for 6 minutes in the presence and absence of a derivative of the D amino acid peptide #1 at various concentrations (at 24° C.) The derivative of D amino acid peptide #1 is identical to D amino acid #1, which is described in Example 3, except it is biotinylated. At a concentration of 2.5 mM, virtually complete inhibition of IgE-Fc binding was observed. The results are shown in FIG. 3.

Example 5

SEQ ID NO:6 is SEQ ID NO:3 with cysteine residues at the N and C terminals. The two cysteines form disulfide bonds which result in the cyclization of the peptide.

D amino acid peptide #1 has the same amino acid sequence as SEQ ID NO:6 except that the C terminus cysteine is a D amino acid. D amino acid peptide #1 is also referred to as cyclo(L-262).

D amino acid peptide #2 has the sequence of D amino acids from amino terminus to carboxy terminus: Cys Tyr Lys Leu Ala Glu Gly Asp Lys Tyr Tyr Ile $CYS_{(L)}$. The C terminus cysteine is an L amino acid. This sequence, also referred to as cyclo(rD-262), is the reverse amino acid sequence of SEQ ID NO:6.

Peptides cyclo(L-262) and cyclo(rD-262) were synthesized and tested for activity. The sequences of the peptides are as follows, cyclo(L-262) CIYYKDGEALKYC$_{(D)}$ (all L amino acids except the carboxy terminal cysteine) and cyclo-(rD-262) CYKLAEGDKYYIC$_{(L)}$ (all D amino acids except carboxy terminal cysteine).

The following scrambled peptides were used as controls: cyclo(rD-scram) CLEADYKGYKYIC$_{(L)}$ (all D amino acids except carboxy terminal cysteine) and cyclo(L-scram) CIYKYGKYDAELC$_{(D)}$ (all L amino acids except the carboxy terminal cysteine).

Peptides were synthesized on an Applied Biosystems 430A fully automated peptide synthesizer using standard fmoc chemistry. Intramolecular disulfides were enriched by an air oxidation refolding procedure carried out at 100 µg/ml in 50 mM ammonium bicarbonate, pH 8.5, stirred overnight at 23° C. Peptides show greater than 95% intramolecular disulfide bonding at the end of this procedure as monitored by Ellman's reagent and HPLC analysis. In addition, matrix assisted laser desorption/ionization mass spectrometry (MALDI-MS) was used to confirm the identity and cyclized status of the peptide product. The intramolecular disulfide cyclized product was then purified by RP-HPLC.

Example 6

Figure 5:
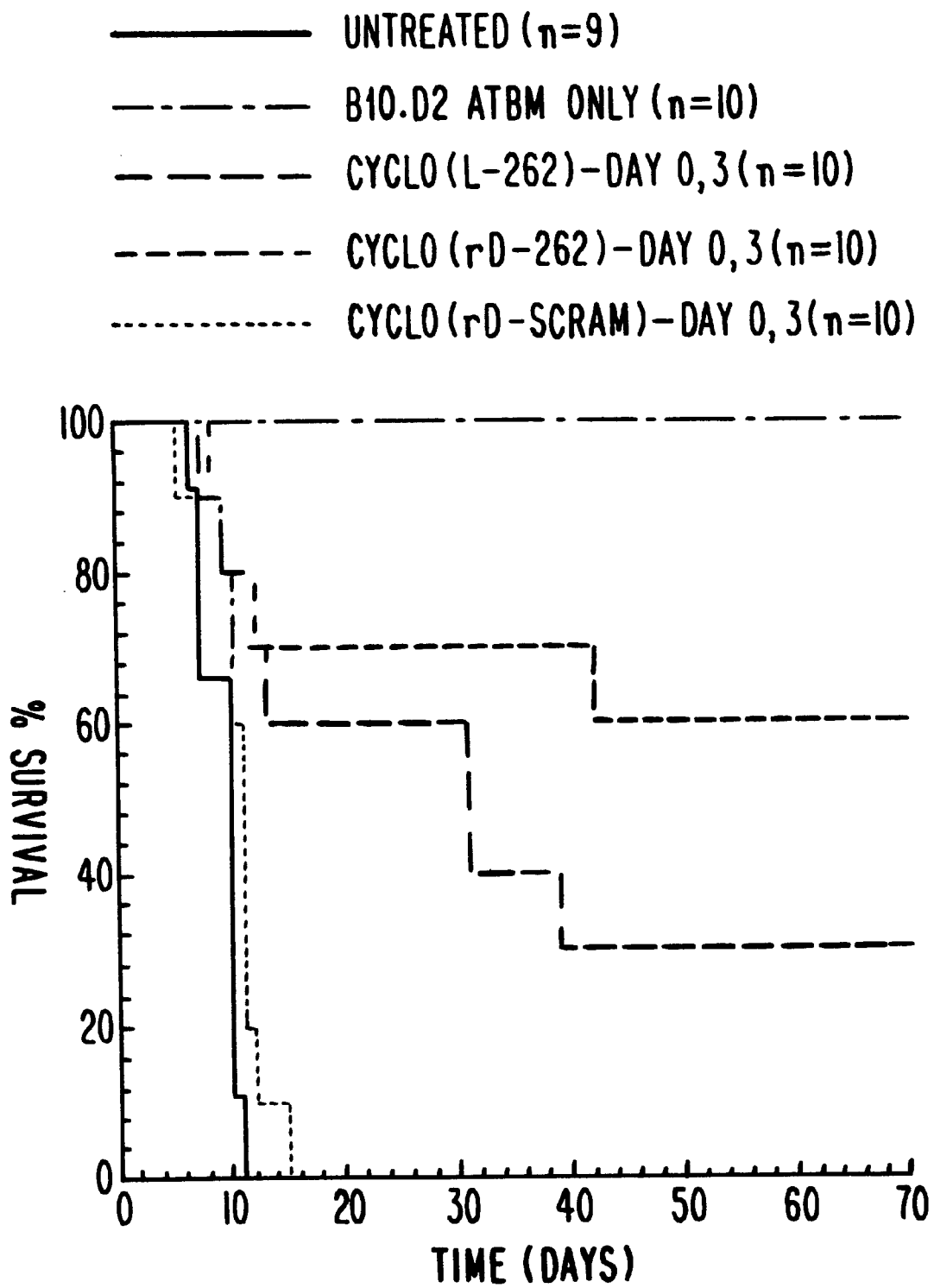
FIG. 5 shows in vivo data that demonstrates inhibition of GVDH by compounds of the invention.

In vivo Inhibition of GVDH (FIG. 5)

Bone marrow cells were obtained from the femurs and tibiae of donor mice by flushing with buffered saline solution (BSS) supplemented with 0.1 bovine serum albumin (Hyclone, Logan, Utah). To prepare anti-Thy-1 (T cell-depleted) bone-marrow (ATBM), cells were incubated with J1J mAb (diluted 1:100) and complement 1:25 for 45 minutes at 37° C., followed by four washes. CD4+ T cell-enriched donor cell populations were prepared by initially treating pooled spleen and lymph node cells with the anti-B cell J11d mAb (diluted 1:5) and complement (1:25) for 1 hour at 37° C. This treatment generally resulted in a population between 90–95% Thy-1+cells, as measured for phenotyping by flow cytometric analysis. These cells were further treated twice with anti-CD8 mAb (3.268, diluted 1:50) plus complement (1:25) for 45 minutes at 37° C., initially and again for 30 minutes with a wash in between. The enriched CD4+ T cells were phenotyped by flow cytometry analysis and were routinely found to be negative for CD8+ T ell subset. For GVHD induction, DBA/2 recipient mice were irradiated 900 cGy by exposure from a Gammacell $^{137}$Cs source (130 cGy/min). Approximately 6 hours later these mice were injected intravenously with donor B10.D2 ATBM cells ($2\times10^6$) alone as a negative control, or a mixture of ATBM ($2\times10^6$) together with $5\times10^6$ CD4+ T cells.

To determine the ability of cyclo(L-262) and cyclo(rD-262) peptides, and scrambled versions of these peptides, to inhibit receptor binding and thereby inhibit GVHD, DBA/2 recipients of B10.D2 CD4+ T-cells were treated on days 0 and 3 with 0.5 mg of peptide i.v. Mice were observed daily for mortality until 70 days post-transplantation and weights were monitored twice weekly. Data are shown in FIG. 5.

Example 7

Figure 6:
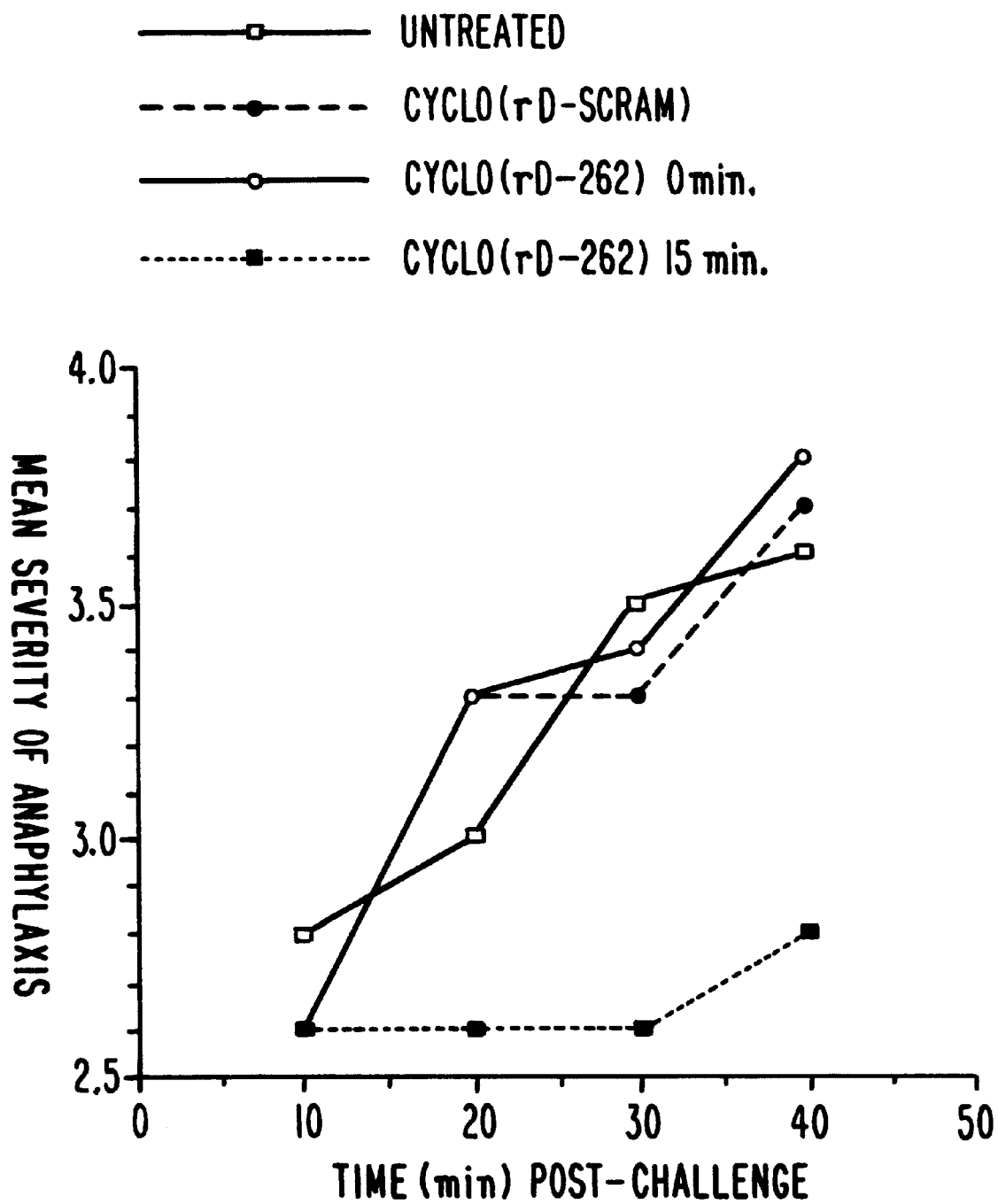
FIG. 6 shows in vivo data that demonstrates inhibition of antigen-induced anaphylaxis by compounds of the invention.

In vivo Inhibition of Antigen-Induced Anaphylaxis (FIG. 6)

BALB/c mice primed to bacteriophage lambda cI repressor peptide 9–29 (ref. J. Exp. Med., 174, 847, 1991), with 200 μg i.p., followed by a secondary boost 3 weeks later. They were subsequently challenged with 250 μg of the same antigen, and scored for level of distress (level 4=severe fatal reaction) for up to 40 minutes after challenge. Cyclo(rD-262) peptide (0.5 mg) was administered at either time 0 or 15 minutes before challenge, and compared with administration of a scrambled version of the peptide at time 0. The results are shown in FIG. 6.

We claim:

1. A peptide consisting of up to 25 amino acids, wherein said peptide
   a) comprises at least a fragment of SEQ ID NO:3 of at least 6 amino acids and
   b) is capable of modulating IgE binding to FcεR1.

2. The peptide of claim 1 wherein said peptide consists of 8–15 amino acids.

3. The peptide of claim 1 wherein said peptide comprises SEQ ID NO:3 or a fragment thereof selected from the group consisting of amino acids 1–6, 2–7, 3–8, 4–9, 5–10, 6–11, 1–7, 2–8, 3–9, 4–10, 5–11, 1–8, 2–9, 3–10, 4–11, 1–9, 2–10, 3–11, 1–10, and 2–11 of SEQ ID NO:3.

4. The peptide of claim 1 wherein said peptide is conformationally restricted.

5. The peptide of claim 1 having the amino acid sequence C—Y—K—L—A—E—G—D—K—Y—Y—I—C, wherein said peptide is constructed of all D amino acids except the amino terminal cysteine.

6. The pharmaceutical composition comprising a peptide of claim 5 and a pharmaceutically acceptable carrier or diluent.

7. A peptide consisting of up to 25 amino acids, wherein said peptide
   a) comprises SEQ ID NO:3 and
   b) is capable of modulating IgE binding to FcεR1.

8. A peptide consisting of up to 25 amino acids, wherein said peptide
   a) comprises at least a fragment of SEQ ID NO:3 of at least 6 amino acids
   b) has an amino terminal cysteine and a carboxy terminal cysteine which are linked by a disulfide bond and
   c) is capable of modulating IgE binding to FcεR1.

9. The peptide of claim 8 having the amino acid sequence: C—I—Y—Y—K—D—G—E—A—L—K—Y—(D)—C, wherein the carboxy terminal cysteine is a "D" amino acid.

10. A pharmaceutical composition comprising a peptide of claim 9 and a pharmaceutically acceptable carrier or diluent.

11. A pharmaceutical composition comprising:
    a) a peptide consisting of up to 25 amino acids, wherein said peptide
       i) comprises at least a fragment of SEQ ID NO:3 of at least 6 amino acids and
       ii) is capable of modulating IgE binding to FcεR1; and
    b) a pharmaceutically acceptable carrier or diluent.

12. A peptide consisting of 6–50 amino acids, wherein said peptide
    a) comprises SEQ ID NO:5 and
    b) is capable of modulating IgE binding to FcεR1.

13. The peptide of claim 12 wherein said peptide consists of 6–20 amino acids.

14. The peptide of claim 12 wherein said peptide consists of 8–15 amino acids.

15. The peptide of claim 12 wherein said peptide comprises SEQ ID NO:4 or a fragment thereof comprising amino acids 7–12, 7–13, 7–14, 7–15, 7–16, 7–17, 7–18, 7–19, 6–12, 6–13, 6–14, 6–15, 6–16, 6–17, 6–18, 6–19, 5–12, 5–13, 5–14, 5–15, 5–16, 5–17. 5–18, 5–19, 4–12, 4–13, 4–14, 4–15, 4–16, 4–17, 4–18, 4–19, 3–12, 3–13, 3–14, 3–15, 3–16, 3–17, 3–18, 3–19, 2–12, 2–13, 2–14, 2–15, 2–16, 2–17, 2–18, 2–19, 1–12, 1–13, 1–14, 1–15, 1–16, 1–17, 1–18 or 1–19 of SEQ ID NO:4.

16. The peptide of claim 12 wherein said peptide is conformationally restricted.

17. The peptide of claim 12 wherein said peptide has an amino terminal cysteine and a carboxy terminal cysteine which are linked by a disulfide bond.

18. A pharmaceutical composition comprising:
   a) a peptide consisting of 6–50 amino acids, wherein said peptide
      i) comprises SEQ ID NO:5 and
      ii) is capable of modulating IgE binding to FcϵR1; and
   b) a pharmaceutically acceptable carrier or diluent.

19. A method of inhibiting IgE binding to FcϵR1 on cells comprising the steps of:
   contacting cells that contain the FcϵR1 with an amount of a peptide sufficient to inhibiting IgE binding to FcϵR1, wherein said peptide
      a) consists of 4–50 amino acids,
      b) comprises at least a fragment of SEQ ID NO:3 of at least 4 amino acids.

20. A method of inhibiting IgE binding to FcϵR1 on cells comprising the steps of:
   contacting cells that contain the FcϵR1 with an amount of a peptide sufficient to inhibit IgE binding to FcϵR1, wherein said peptide
      a) consists of 6–50 amino acids,
      b) comprises SEQ ID NO:5.

21. A method of therapeutically or prophylactically treating an individual suspected of suffering from or being susceptible to an immediate allergic response comprising the steps of:
   administering to said individual an effective amount of a peptide which:
      a) consists of 4–50 amino acids,
      b) comprises at least a fragment of SEQ ID NO:3 of at least 4 amino acids, and
      c) inhibits IgE binding to FcϵR1.

22. The method of claim 21 wherein said immediate allergic response is selected from the group consisting of: graft versus host disease, allergic rhinitis, food allergies, atropic dermatitis and allergic asthma.

23. A method of therapeutically or prophylactically treating an individual suspected of suffering from or being susceptible to an immediate allergic response comprising the steps of:
   administering to said individual an effective amount of a peptide which:
      a) consists of between 6 and 50 amino acids,
      b) comprises SEQ ID NO:5, and
      c) inhibits IgE binding to FcϵR1.

24. The method of claim 23 wherein said immediate allergic response is selected from the group consisting of: graft versus host disease, allergic rhinitis, food allergies, atropic dermatitis and allergic asthma.

25. A peptide dimer comprising a first monomer and a second monomer wherein
   a) said first monomer
      i) consists of 4–50 amino acids,
      ii) comprises at least a fragment of SEQ ID NO:3 of at least 4 amino acids and
   b) said second monomer
      i) consists of 6–50 amino acids,
      ii) comprises SEQ ID NO:5;
wherein said dimer is capable of inhibiting IgE binding to FcϵR1.

26. A peptide consisting of amino and carboxy terminal cysteines flanking SEQ ID NO:3 or a fragment thereof selected from the group consisting of amino acids 1–4, 2–5, 3–6, 4–7, 5–8, 6–9, 7–10, 8–11, 1–5, 2–6, 3–7, 4–8, 5–9, 6–10, 7–11, 1–6, 2–7, 3–8, 4–9, 5–10, 6–11, 1–7, 2–8, 3–9, 4–10, 5–11, 1–8, 2–9, 3–10, 4–11, 1–9, 2–10, 3–11, 1–10, and 2–11 of SEQ ID NO:3.

27. A pharmaceutically composition comprising:
   a) a peptide of claim 26 and
   b) a pharmaceutically acceptable carrier or diluent.

28. The peptide of claim 26 wherein said peptide consists of amino and carboxy terminal cysteines flanking SEQ ID NO:3 or a fragment thereof selected from the group consisting of amino acids 1–6, 2–7, 3–8, 4–9, 5–10, 6–11, 1–7, 2–8, 3–9, 4–10, 5–11, 1–8, 2–9, 3–10, 4–11, 1–8, 2–9, 3–10, 4–11, 1–9, 2–10, 3–11, 1–10, and 2–11 of SEQ ID NO:3.

29. A pharmaceutically composition comprising:
   a) a peptide of claim 28 and
   b) a pharmaceutically acceptable carrier or diluent.

* * * * *

UNITED STATES PATENT AND TRADEMARK OFFICE
CERTIFICATE OF CORRECTION

PATENT NO. : 5,962,634
DATED : October 5, 1999
INVENTOR(S) : Bradford A. Jameson et al It is certified that error appears in the above-identified patent and that said Letters Patent is hereby corrected as shown below:

Col. 2, line 14, "CE3" should be --$C_E3$--

Col. 2, line 48, "on" should have a space between the word.

Col. 23, line 13, "inhibiting" should be --inhibit--

Signed and Sealed this

Twenty-seventh Day of March, 2001

Attest:

NICHOLAS P. GODICI

Attesting Officer

Acting Director of the United States Patent and Trademark Office